United States Patent
Trivedi et al.

(10) Patent No.: US 10,174,057 B2
(45) Date of Patent: Jan. 8, 2019

(54) METALLACROWN COMPLEXES AND METHODS OF MAKING THE SAME

(71) Applicants: THE REGENTS OF THE UNIVERSITY OF MICHIGAN, Ann Arbor, MI (US); Centre National De La Recherche Scientifique, Paris (FR)

(72) Inventors: Evan R. Trivedi, Farmington Hills, MI (US); Vincent L. Pecoraro, Ann Arbor, MI (US); Svetlana V. Eliseeva, Orleans (FR); Stephane Petoud, Paris (FR); Joseph Jankolovits, Oakland, CA (US); Alexandra Foucault-Collet, San Diego, CA (US); Ivana Martinic, Orleans (FR)

(73) Assignees: The Regents of The University of Michigan, Ann Arbor, MI (US); Centre National De La Recherche Scientifique, Paris (FR)

( * ) Notice: Subject to any disclaimer, the term of this patent is extended or adjusted under 35 U.S.C. 154(b) by 0 days.

(21) Appl. No.: 14/916,822

(22) PCT Filed: Sep. 5, 2014

(86) PCT No.: PCT/US2014/054335
§ 371 (c)(1),
(2) Date: Mar. 4, 2016

(87) PCT Pub. No.: WO2015/035196
PCT Pub. Date: Mar. 12, 2015

(65) Prior Publication Data
US 2016/0215001 A1    Jul. 28, 2016

Related U.S. Application Data

(60) Provisional application No. 61/874,659, filed on Sep. 6, 2013.

(51) Int. Cl.
*C07F 5/00*    (2006.01)
*G01N 21/64*   (2006.01)

(52) U.S. Cl.
CPC ......... *C07F 5/003* (2013.01); *G01N 21/6428* (2013.01); *G01N 21/6458* (2013.01); *G01N 2201/061* (2013.01)

(58) Field of Classification Search
CPC .......... G01N 21/6428; G01N 21/6458; G01N 2201/061
See application file for complete search history.

(56) References Cited

FOREIGN PATENT DOCUMENTS

WO    WO 2006/001835    1/2006

OTHER PUBLICATIONS

Trivedi; Journal of the American Chemical Society; 2014, 136, 1526-1534.*
Jankolovits, Joseph, et al. "Using the structural versatility of lanthanide metallacrowns to tune anion recognition, self-assembly, and luminenscence properties" Dissertation, 2012, URL:http:f/hdl.handle.net/2027.42/93877.
Jankolovits, Joseph, et al. "Assembly of near-infrared luminescent lanthanide hose (host-guest) complexes with a metallacrown sandwich motif" Angewandte Chemie International Edition, vol. 50; No. 41; 2011; pp. 9660-9664.
International Search Report and Written opinion for International Application No. PCT/US2014/054335 dated Oct. 24, 2014, 10 pages.

* cited by examiner

*Primary Examiner* — Pancham Bakshi
(74) *Attorney, Agent, or Firm* — Dierker & Kavanaugh, P.C.

(57) ABSTRACT

A metallacrown complex has the formula: Ln(III)[12-MC-4]2[24-MC-8], wherein MC is a metallacrown macrocycle with a repeating sub-unit consisting of a transition metal (M(II)) and a hydroxamic acid (HA) ligand that produces a ligand-based charge transfer state when incorporated into the metallacrown complex. In an example of a method for making the metallacrown complex, a hydroxamic acid (HA) ligand that is to produce a ligand-based charge transfer state when incorporated into the metallacrown complex, a transition metal salt, and a rare-earth salt are dissolved in a solvent to form a solution. A base is added to the solution. The solution is stirred at a predetermined temperature for a predetermined time. The solution is exposed to a purification method to produce crystals of the metallacrown complex.

15 Claims, 9 Drawing Sheets

METALLACROWN COMPLEXES AND METHODS OF MAKING THE SAME

CROSS-REFERENCE TO RELATED APPLICATIONS

This application claims the benefit of U.S. Provisional Application Ser. No. 61/874,659, filed Sep. 6, 2013.

STATEMENT REGARDING FEDERALLY SPONSORED RESEARCH OR DEVELOPMENT

This invention was made with government support under Grant No. 1057331 awarded by the National Science Foundation (NSF). The Government has certain rights in the invention.

BACKGROUND

Optical devices, bioanalytical assays, and biological imaging probes often utilize components that exhibit optical properties, such as organic fluorophores and semi-conductor nanoparticles. Some desired optical properties include long luminescence lifetimes, large effective energy differences between excitation and emission bands, and sharp emission bands throughout the visible and near-infrared (NIR) spectral ranges. Lanthanide ions ($Ln^{3+}$) contain unique 4f orbitals and exhibit unique luminescent characteristics that include sharp emission bands throughout the visible and near-infrared (NIR) spectral regions. However, the f-f transitions of $Ln^{3+}$ ions are Laporte forbidden with low absorption coefficients, resulting in inefficient direct excitation and requiring sensitization with an appropriate antenna.

BRIEF DESCRIPTION OF THE DRAWINGS

Features and advantages of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 8A is the brightfield image and FIG. 8B is the emission signal image in the NIR range (long pass 805 nm filter) obtained after 500 ms of exposure to excitation ($\lambda_{ex}$=377 nm with 50 nm band pass filter);

FIG. 8D is the brightfield image and FIG. 8E is the autofluorescence signal image in the NIR range (long pass 805 nm filter) obtained after 500 ms of exposure to excitation ($\lambda_{ex}$=377 nm with 50 nm band pass filter);

FIG. 9A is the brightfield image and FIG. 9B is the emission signal image in the NIR range (long pass 805 nm filter) obtained after 800 ms of exposure to excitation ($\lambda_{ex}$=377 nm with 50 nm band pass filter);

FIG. 10A is the brightfield image and FIG. 10B is the emission signal image in the NIR range (long pass 805 nm filter) obtained after 13 s of exposure to excitation ($\lambda_{ex}$=377 nm with 50 nm band pass filter);

FIG. 11A is the brightfield image and FIG. 11B is the emission signal image in the NIR range (long pass 805 filter nm) obtained after 13 s of exposure to excitation ($\lambda_{ex}$=377 nm 50 nm band pass filter)

DETAILED DESCRIPTION

Figure 1A:
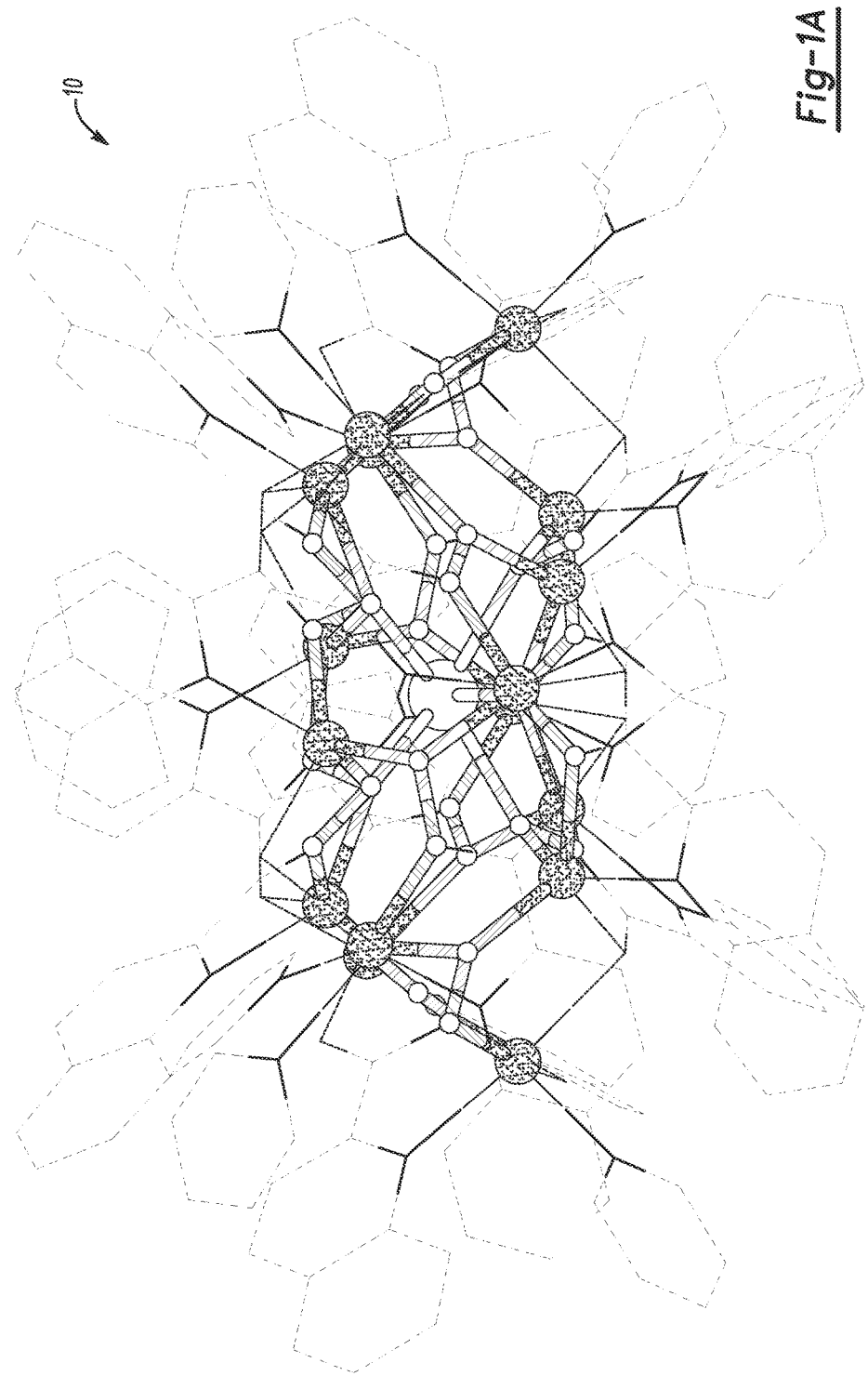
FIGS. 1A and 1B are black and white representations of X-ray crystal structures of $Dy^{3+}[12\text{-}MC\text{-}4]_2[24\text{-}MC\text{-}8]$ along the a-axis and the c-axis, respectively.

Metallacrowns are metal complexes made with tetradentate ligands that cyclize to form a repeating $[MNO]_x$ sub-unit, where M is a transition metal ion. Similar to crown ethers, metallacrowns can be synthesized with a range of sizes, and the inward facing oxygen atoms are capable of binding to a central metal ion (i.e., coordinate central metal). The example metallacrown complexes disclosed herein are three-component supramolecular assemblies with transition metals ($M^{2+}$), tetra-dentate hydroxamic acid ligands ($L^{2-}$)

that are capable of transferring energy to a central ion and/or producing a ligand-based charge transfer state when incorporated into the metallacrown complex, and lanthanide ions (Ln$^{3+}$) or other rare-earth metal ions.

In particular, the examples disclosed herein utilize the tetra-dentate ligand quinaldichydroxamic acid:

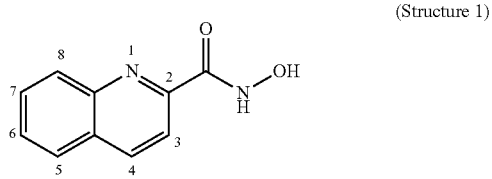 [SMILES: O=C(NO)c1ccc2ccccc2n1]

(Structure 1)

or a derivative thereof. Examples of suitable quinaldichydroxamic acid derivatives may include any combination of R-groups bound to positions 3 through 8 as shown in Structure 1 above. In an example, the R-groups are independently selected from —H, —D (deuterium), —OH, —SH, —NH$_2$, —NO$_2$, —F, —Cl, —Br, —I, —CF$_3$, —OCH$_3$, —SO$_3$H, —CH$_3$, and CN. In another example, the R-group at any of positions 3 through 8 of Structure 1 may also be a fused aromatic ring. Examples of the fused aromatic ring include benzene, naphthalene, phenanthrene, chrysene, or pyrene. It is to be understood that each position on the fused aromatic ring may also have R-groups bound thereto (e.g., —H, —D (deuterium), —OH, etc.). In yet a further example, the R-group at any of positions 3 through 8 of Structure 1 may also be a fused heterocyclic ring. Examples of the fused heterocyclic ring include furan, thiophene, pyrrole, pyridine, imidazole, thiazole, pyrimidine, indole, isoindole, indolizine, purine, carbazole, dibenzofuran, oxazole, or isoxazole. It is to be understood that each position on the fused heterocycle may also have R-groups bound thereto (e.g., —H, —D (deuterium), —OH, etc.). In still another example, the R-group(s) of Structure 1 may be amides, or chromophoric or recognition regions, such as biotin, sugar, oligos, peptides (e.g., RGD), antibodies, or the like. In still other examples, the R groups may be =O, =N, —N$_3$, —NR'H, —NR'$_2$, —NR'$^{3+}$, —COOH, —COOR', —CH$_2$—R', —CHR$_2$, —CHR'R'', —CR'R''R''', —OR', or the like, where R', R'', and R''' may be independently selected from any of the aforementioned R-groups.

Examples of other derivatives include heterocycles derived from quinaldichydroxamic acid with nitrogen, oxygen or sulfur (instead of carbon) at positions 3 to 8. It is to be understood that these derivatives could contain nitrogen, oxygen or sulfur atoms individually or in combination at positions 3 to 8.

This ligand or a derivative thereof provides the complexes with a unique molecular structure. In addition, this ligand or a derivative thereof efficiently absorbs excitation light and transfers the resulting energy to the Ln$^{3+}$ ion. It has been unexpectedly found that the metallacrown complexes formed with the quinaldichydroxamic acid ligand or a derivative thereof provide a combination of a near-visible ligand-based charge transfer absorption, remarkably high quantum yields (exhibiting intense near-infrared luminescence), and long luminescence lifetimes. Complexes with these properties may be used in a variety of applications, such as bioanalytical assays, biological imaging, biomedical analysis, telecommunications (e.g., erbium-doped fiber amplifiers), energy conversion, photovoltaics, display technology (e.g., as an electroluminescent material in organic light-emitting diodes, OLEDs), security printing (e.g., as components in security inks, counterfeiting tags, barcodes or other identifying codes), and optical materials. For OLEDs, the complexes may be incorporated into a polymer matrix, e.g., to ensure electron conduction. For any application, the R-groups may be selected to modify the solubility or amphiphilicity of the metallacrown complex for the formulation in which the metallacrown complex is being used.

The metallacrown complex disclosed herein has the formula Ln(III)[12-MC-4]$_2$[24-MC-8]. Generally, the MC is a metallacrown macrocycle with a repeating sub-unit consisting of a divalent transition metal ion (M(II) or M$^{2+}$) and the previously mentioned hydroxamic acid ligand (HA) (which, as referred to herein includes quinaldichydroxamic acid or a derivative thereof).

The Ln(III) is a central ion that bonds (e.g., via coordination bonding) to the capping crowns of [12-MC-4]. It is to be understood that Ln$^{3+}$ may include any lanthanide ion, such as dysprosium (Dy$^{3+}$), ytterbium (Yb$^{3+}$), neodymium (Nd$^{3+}$), gadolinium (Gd$^{3+}$), terbium (Tb$^{3+}$), europium (Eu$^{3+}$), erbium (Er$^{3+}$), lanthanum (La$^{3+}$), cerium (Ce$^{3+}$), praseodymium (Pr$^{3+}$), promethium (Pm$^{3+}$), samarium (Sm$^{3+}$), holmium (Ho$^{3+}$), thulium (Tm$^{3+}$), or lutetium (Lu$^{3+}$). Throughout the application, the "Ln$^{3+}$", "Ln(III)", or "lanthanide" may be replaced with other rare-earth metal ions, such as yttrium (Y$^{3+}$) and scandium (Sc$^{3+}$).

The metallacrown complex includes the two capping crowns, each of which is referred to as [12-MC-4]. Example structures of the [12-MC-4] capping crowns are shown below, with 50% thermal displacement parameters and a partial numbering scheme:

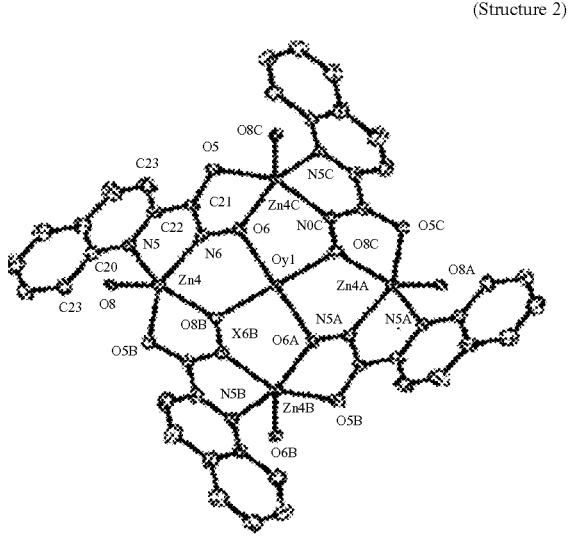

(Structure 2)

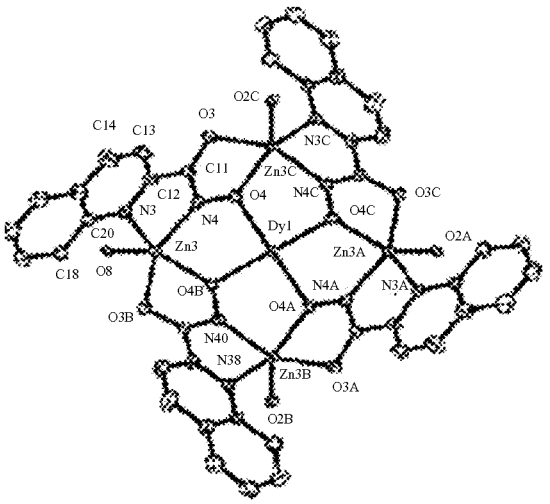

(Structure 3)

Structures 2 and 3 illustrate the Ln(III) ion (in these examples Dy) bonded to the four inward-facing hydroximate oxygen atoms of each capping crown. In structure 2, these inward-facing hydroximate oxygen atoms are labeled O6, O6A, O6B and O6C, and in structure 3, these inward-facing hydroximate oxygen atoms are labeled O4, O4A, O4B and O4C. During the method of making the metallacrown complex (discussed below), the HA ligand cyclizes to form a repeating [M(II)HA] sub-unit, which in [12-MC-4], is repeated four times. As a result, each [12-MC-4] capping crown has twelve total atoms (i.e., 4 Zn, 4 O, and 4 N) in its macrocyclic ring.

The metallacrown complex also includes an encapsulating crown, [24-MC-8]. An example structure of the [24-MC-8] encapsulating crown is shown below, with 50% thermal displacement parameters and a partial numbering scheme:

(Structure 4)

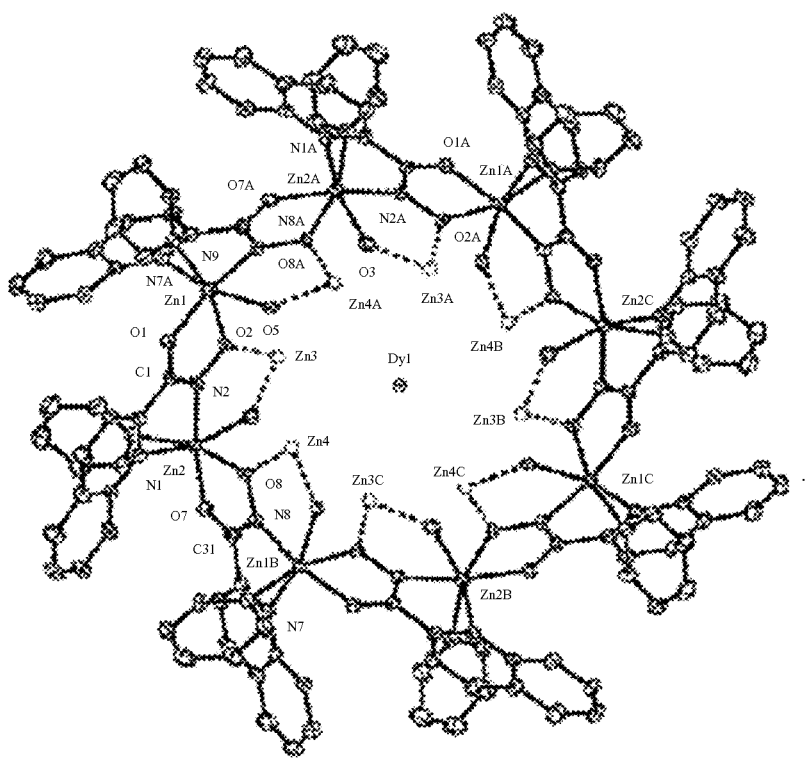

In this example, the HA ligand cyclizes to form the repeating [M(II)HA] sub-unit, which in [24-MC-8] is repeated eight times. As a result, each [24-MC-8] encapsulating crown has twenty-four total atoms (i.e., 8 Zn, 8 O, and 8 N) in its macrocyclic ring.

Structure 4 also illustrates the non-bonded central Ln(III) ion (e.g., Dy1). The dashed lines indicate how the central crown bridges to the smaller, concave, capping crowns (Structures 2 and 3).

As will be discussed below, the method used to form the metallacrown complex may utilize pyridine or some other solvent (e.g., dimethylformamide or methanol), and thus the encapsulating crown (Structure 4) may also have eight pyridine rings, or some other coordinating solvent molecules, attached thereto.

The divalent transition metal may be any transition metal (II) ion. In the examples disclosed herein, $Zn^{2+}$ is the transition metal ion used. The coordination geometry of $Zn^{2+}$ in [24-MC-8] (A) and in [12-MC-4] (B) is shown below:

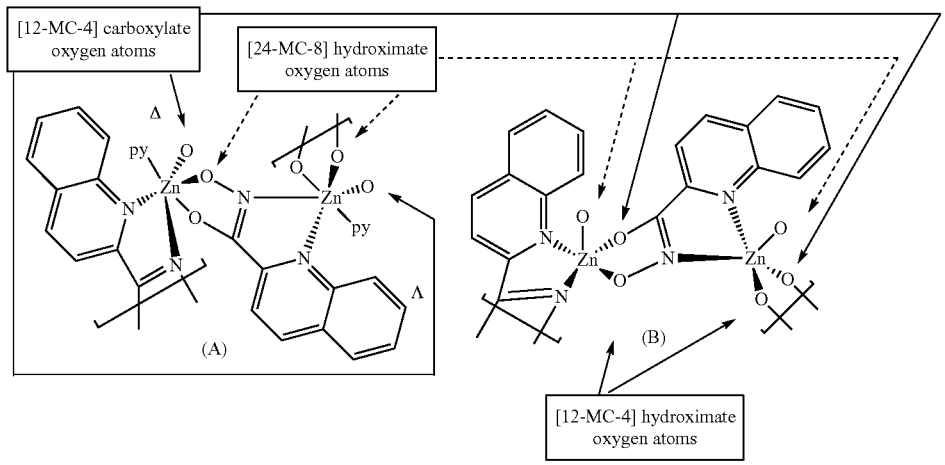

The coordination geometry of $Zn^{2+}$ indicates that the distinct metallacrown rings are linked through bridging oxygen atoms, namely the [12-MC-4] carboxylate oxygen atoms (identified with solid arrows) and the [24-MC-8] hydroximate oxygen atoms (identified with dashed arrows). In other words, the [24-MC-8] unit has a cavity at its center, and the sandwich complex formed between the $Ln^{3+}$ ion and the two [12-MC-4] units is bound within that cavity through the bridging oxygen atoms. As illustrated in (B) above, the $Ln^{3+}$ ion is bound to the [12-MC-4] hydroximate oxygen atoms (identified by dotted arrows).

Figure 1B:
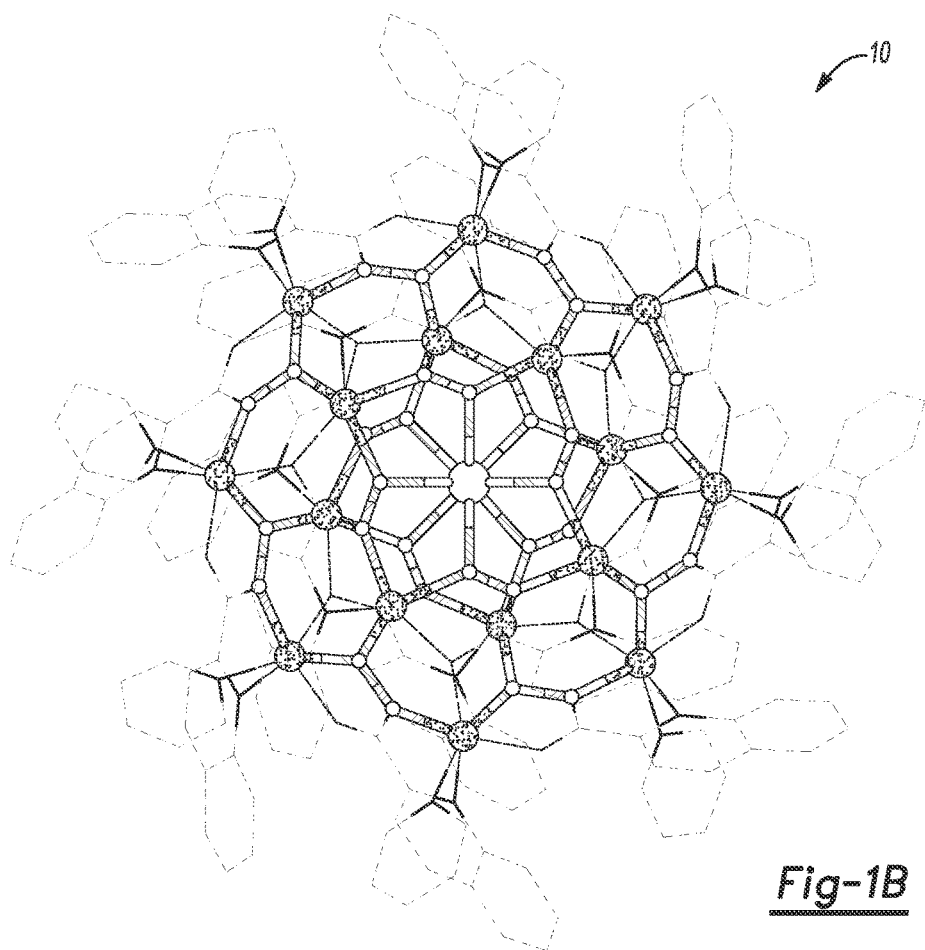

FIGS. 1A and 1B illustrate black and white representations of the X-ray crystal structures of one example of the metallacrown complex 10 (i.e., $Dy^{3+}$[12-MC-4]$_2$[24-MC-8]), viewed along the a-axis (FIG. 1A) and the c-axis (FIG. 1B). The $Dy^{3+}$ ion is shown as a large unhatched sphere at the center of the complex 10 with unhatched bonds attached thereto, the oxygen atoms are shown as smaller unhatched spheres with left slanted cross-hatched bonds (e.g., ) attached thereto or are represented by the intersection of short dashed line bonds (e.g., ), the nitrogen atoms are shown as smaller unhatched spheres with right slanted cross-hatched bonds and/or solid bold line bonds (e.g., ) attached thereto or are represented by the intersection of bold solid line bonds (e.g., ), the $Zn^{2+}$ ions are shown as speckled spheres with speckled bonds and/or solid line bonds attached thereto (e.g., ), and the rings of the HA ligands and the pyridine ligands are shown as dashed lines (e.g., ). It is to be understood that the HA ligands may have slightly different structures depending upon which HA ligand is selected.

In an example of the method for making the metallacrown complex, an example of the HA ligand that is capable of producing a ligand-based charge transfer state when incorporated into the metallacrown complex, a transition metal salt, and a rare-earth metal salt are dissolved in a solvent to form a solution. Example solvents include dimethylformamide (DMF), methanol, water, and combinations thereof.

The HA ligand (i.e., quinaldichydroxamic acid or a derivative thereof) may be prepared in a single step. In an example, fresh hydroxylamine is first prepared by combining hydroxylamine hydrochloride and potassium hydroxide in methanol at about 0° C. This solution may be stirred (e.g., for about 20 minutes or longer) and filtered to remove potassium chloride. Quinaldic acid and N-methylmorpholine are combined with stirring in dichloromethane. This solution may be cooled to about 0° C., at which time ethylchloroformate is added. This reaction may be stirred for about 20 minutes to 1 hour, and then filtered. The hydroxylamine solution is added to the filtrate at about 0° C. This reaction mixture may be allowed to warm to room temperature and stirred for about 1.5 hours. The volume may then be reduced to about 200 mL en vacuo and water is added to induce the precipitation of a white solid. The solid is collected by filtration, and may be triturated with hot (about 40° C.) dichloromethane to yield quinaldichydroxamic acid as a white powder.

Any transition metal salt may be used. In an example, the transitional metal salt is a triflate, a mesylate, a besylate, a camsylate, an edisylate, an estolate, an esylate, a napsylate, a tosylate, a fluoride, a chloride, a bromide, an iodide, a nitrate, a sulfate, a carbonate, an acetate, a sulfonate, or a phosphate of any of $Co^{2+}$, $Ni^{2+}$, $Cu^{2+}$, $Zn^{2+}$, $Rh^{2+}$, $Pd^{2+}$, $Ag^{2+}$, $Cd^{2+}$, $Ir^{2+}$, $Pt^{2+}$, $Au^{2+}$, or $Hg^{2+}$.

The rare-earth metal salt may be a triflate, a mesylate, a besylate, a camsylate, an edisylate, an estolate, an esylate, a napsylate, a tosylate, a fluoride, a chloride, a bromide, an iodide, a nitrate, a sulfate, a carbonate, an acetate, a sulfonate, or a phosphate of any of $Y^{3+}$, $Sc^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, or $Lu^{3+}$.

As mentioned above, the HA ligand, the transition metal salt, and the rare-earth metal salt are dissolved in the solvent to form a solution. A base is then added to the solution. Examples of suitable bases include triethylamine (TEA), trimethylamine, or other Bronsted bases. In an example, when the base is added to the solution, the resulting reaction mixture turns yellow.

The reaction mixture (i.e., the solution and the base) is then stirred for a predetermined time at a predetermined temperature. In an example, the temperature is room temperature (e.g., from about 18° C. to about 22° C.) and the time ranges from about 12 hours to about 24 hours.

The reaction mixture is then exposed to a purification method to produce the highly pure metallacrown complex. Examples of suitable purification methods include recrystallization by slow evaporation of the solvent, recrystallization by vapor diffusion, recrystallization by solvent layering, high-performance liquid chromatography (HPLC), or flash chromatography. In one example, pyridine is used in the purification process, which results in the introduction of pyridine ligands to the metallacrown complex 10.

It is to be understood that the properties of the resulting metallacrown complex (e.g., the excitation wavelength) may be tuned by the selection of the ligand. For example, a different quinaldichydroxamic acid derivative may be incorporated in the metallacrown complex to alter the excitation wavelength of the resulting metallacrown complex. It is believed that changing the substituent on the metallacrown complex will induce change in its electronic structure and to the corresponding excitation wavelengths.

A charge balance of the metallacrown complex 10 that is formed may be obtained by the presence of a negatively charged species, such as an unbound counterion (e.g., triflate(s), mesylate(s), besylate(s), camsylate(s), edisylate(s), estolate(s), esylate(s), napsylate(s), tosylate(s), fluoride(s), chloride(s), bromide(s), iodide(s), nitrate(s), sulfate(s), carbonate(s), acetate(s), sulfonate(s), or phosphate(s)).

The $Ln(III)[12\text{-}MC\text{-}4]_2[24\text{-}MC\text{-}8]$ metallacrown complexes disclosed herein exhibit desirable absorption ($\varepsilon[380\text{ nm}] \approx 5.5 \cdot 10^4$ $M^{-1}cm^{-1}$). It is believed that this is due to the ligand-based charge transfer state of the bound HA ligands. Excitation through this ligand-based charge transfer state is believed to lead to remarkably high luminescence quantum yields that result from several parameters, including efficient sensitizer to lanthanide energy transfer and protection of the $Ln^{3+}$ ion from the solvent environment. Luminescence quantum yields reported herein in the following examples are believed to be unmatched for $Nd^{3+}$ and $Er^{3+}$ complexes with organic ligands containing C—H bonds.

Because the $Ln(III)[12\text{-}MC\text{-}4]_2[24\text{-}MC\text{-}8]$ metallacrown complexes exhibit desirable absorption, the $Ln(III)[12\text{-}MC\text{-}4]_2[24\text{-}MC\text{-}8]$ metallacrown complexes may be useful as an optical imaging agent in biological or other experimental conditions. In these instances, the $Ln(III)[12\text{-}MC\text{-}4]_2[24\text{-}MC\text{-}8]$ metallacrown complexes may be incorporated into a liquid carrier or a solid carrier. For example, the $Ln(III)[12\text{-}MC\text{-}4]_2[24\text{-}MC\text{-}8]$ metallacrown complexes may be incorporated into a solution (e.g., DMF, dimethyl sulfoxide (DMSO), methanol, ethanol, water, and combinations thereof) or a bead of another composition (e.g., latex, silica, polystyrene, etc.), and then added to a medium containing cells. The incubated cells may then be analyzed using any suitable optical imaging technique, such as epifluorescence microscopy or confocal fluorescence microscopy.

The beads are to protect the metallacrown complex from the external environment, and to allow vectorization of the metallacrown complex. The beads that the $Ln(III)[12\text{-}MC\text{-}4]_2[24\text{-}MC\text{-}8]$ metallacrown complexes are incorporated into may be polymer beads or silica beads. Examples of polymer beads include those formed from acryl and/or vinyl-containing monomers, for example, methacrylate, styrene, etc. Other examples of polymer beads include poly(lactic acid) beads. Any examples of the beads may be functionalized with different groups suitable for coupling with specific targeting moieties. As such, in some examples, incorporating the $Ln(III)[12\text{-}MC\text{-}4]_2[24\text{-}MC\text{-}8]$ metallacrown complexes into beads enables control over selective detection of targeting moieties. The beads may be coated on their surfaces either by —$NH_2$ or —COOH groups, which allows for facile conjugation to targeting moieties, such as peptide, proteins, antibodies, oligonucleotides, sugars. In an example, the metallacrown complex is incorporated into the bead by dissolving the metallacrown complex in a suitable solvent at an appropriate concentration, and then incubating the solution with the beads. After a suitable incubation time, the metallacrown complex loaded beads may be collected from the solution through any suitable technique, such as centrifugation and decanting.

To further illustrate the present disclosure, examples are given herein. It is to be understood that these examples are provided for illustrative purposes and are to be construed as non-limiting.

EXAMPLES

Preparation of Quinaldichydroxamic Acid

Quinaldichydroxamic acid was made by first preparing fresh hydroxylamine. The fresh hydroxylamine was prepared by combining hydroxylamine hydrochloride (12.0 g, 173 mmol) and potassium hydroxide (11.4 g, 173 mmol) in methanol (200 mL) at 0° C. The solution was stirred for 20 minutes, filtered to remove potassium chloride, and set aside. Meanwhile, quinaldic acid (20.0 g, 116 mmol) and N-methylmorpholine (14.0 mL, 127 mmol) were combined with stirring in dichloromethane (300 mL). This solution was cooled to 0° C., at which time ethylchloroformate (12.1 mL, 127 mmol) was added. This reaction was stirred for 20 minutes, and then filtered. The hydroxylamine solution was added to the filtrate at 0° C. This reaction mixture was allowed to warm to room temperature and was stirred for 1.5 hours. The volume was reduced to about 200 mL en vacuo and water (1 L) was added to induce the precipitation of a white solid. The solid was collected by filtration and triturated with hot dichloromethane (800 mL) to yield quinaldichydroxamic acid (12.7 g, 58.2%) as a white powder. M.p. 146-148° C. Electrospray ionization-mass spectroscopy (ESI-MS), calc. for $[M+H^+]$, $C_{10}H_9N_2O_2$, 189.1; found 189.1; calc. for $[M+Na^+]$, $C_{10}H_8N_2NaO_2$, 211.0; found 211.1. $^1H$ NMR (400 MHz, DMSO-$d_6$) δ11.51 (s, 1 H), 9.18 (s, 1 H), 8.53 (d, J=8.5 Hz, 1 H), 8.09-8.04 (m, 3H), 7.84 (m, 1 H), 7.69 (m, 1H). $^{13}C$ NMR (100 MHz, DMSO-$d_6$) δ161.7, 150.3, 146.0, 137.6, 130.4, 129.2, 128.6, 128.0, 127.9, 118.7. Elem. Anal., calc. (found) for $(C_{10}H_8N_2O_2)(H_2O)$, C: 58.25 (58.25), H: 4.89 (4.94), N: 13.59 (13.65). UV-vis (MeOH), $\lambda_{max}$, nm (log ε) 207 (4.4), 238 (4.5), 300(br) (3.5).

Preparation of $Ln^{3+}[12\text{-}MC\text{-}4]_2[24\text{-}MC\text{-}8]$

Several metallacrown complexes were prepared according to the method disclosed herein.

$DyZn_{16}(quinHA)_{16}(OTf)_3$ (i.e., $Dy^{3+}[12\text{-}MC\text{-}4]_2[24\text{-}MC\text{-}8]$ with $(OTf)_3$, 5 water molecules, and 3 DMF molecules) was prepared by dissolving quinaldichydroxamic acid (200 mg, 1.06 mmol), zinc triflate (385 mg, 1.06 mmol), and dysprosium triflate (81 mg, 0.13 mmol) in 15 mL dimethylformamide. Triethylamine (296 μL, 2.12 mmol) was added. The solution immediately turned yellow and was stirred at room temperature overnight. The solution was then set aside for slow evaporation, which produced yellow plate crystals within two weeks. The crystals were collected by filtration and air dried to yield $DyZn_{16}(quinHA)_{16}(OTf)_3$ (29 mg, 8.4%). ESI-MS, calc. for $[M]^{3+}$, $C_{160}H_{96}DyN_{32}O_{32}Zn_{16}$, 1395.8; found 1395.7. Elem. Anal., calc. (found) for $(C_{163}H_{96}DyF_9N_{32}O_{41}S_3Zn_{16})(H_2O)_5(C_3H_7NO)_3$, C: 41.79 (41.81), H: 2.59 (2.81), N: 9.92 (10.23).

A similar process was used to form $YZn_{16}(quinHA)_{16}(OTf)_3$ (i.e., $Y^{3+}[12\text{-}MC\text{-}4]_2[24\text{-}MC\text{-}8]$ with $(OTf)_3$, 5 water molecules, and 3 DMF molecules) (96 mg, 28%), except that yttrium triflate (70 mg, 0.13 mmol) was used. ESI-MS, calc. for $[M]^{3+}$, $C_{160}H_{96}N_{32}O_{32}YZn_{16}$, 1371.1; found 1371.2. $^1H$ NMR (400 MHz, $CD_3OD$) δ8.36 (d, J=4.7 Hz, 8 H), 8.34 (d, J=4.7 Hz, 8 H), 8.22 (d, J=8.5 Hz, 8 H), 8.09 (d, J=8.5 Hz, 8 H), 7.73 (d, J=7.6 Hz, 8 H), 7.52 (d, J=8.5 Hz, 8 H), 7.49 (d, J=8.0 Hz, 8 H), 7.25 (m, 16 H), 7.19 (d, J=8.5 Hz, 8 H), 7.09 (m, 8 H), 6.95 (m, 8 H). Elem. Anal., calc. (found) for $(C_{163}H_{96}F_9N_{32}O_{41}S_3YZn_{16})(H_2O)_5(C_3H_7NO)_3$, C: 42.42 (42.48), H: 2.63 (2.90), N: 10.07 (10.40).

A similar process was also used to form $YbZn_{16}(quinHA)_{16}(OTf)_3$ (i.e., $Yb^{3+}[12\text{-}MC\text{-}4]_2[24\text{-}MC\text{-}8]$ with $(OTf)_3$, 5 water molecules, and 3 DMF molecules) (96 mg, 28%), except that ytterbium triflate (81 mg, 0.13 mmol) was used. ESI-MS, calc. for $[M]^{3+}$, $C_{160}H_{96}N_{32}O_{32}YbZn_{16}$, 1399.3; found 1399.4. Elem. Anal., calc. (found) for ($C_{163}H_{96}F_9N_{32}O_{41}S_3YbZn_{16}$)($H_2O$)$_5$($C_3H_7NO$)$_3$, C: 41.70 (41.73), H: 2.58 (2.74), N: 9.89 (9.98).

A similar process was also used to form NdZn$_{16}$(quinHA)$_{16}$(OTf)$_3$ (i.e., Nd$^{3+}$[12-MC-4]$_2$[24-MC-8] with (OTf)$_3$, 5 water molecules, and 3 DMF molecules) (58 mg, 34%), except that neodymium triflate (77 mg, 0.13 mmol) was used. ESI-MS, calc. for [M]$^{3+}$, $C_{160}H_{96}N_{32}NdO_{32}Zn_{16}$, 1389.7; found 1389.2. Elem. Anal., calc. (found) for ($C_{163}H_{96}F_9N_{32}NdO_{41}S_3Zn_{16}$)($H_2O$)$_5$($C_3H_7NO$)$_3$, C: 41.94 (41.76), H: 2.60 (2.76), N: 9.95 (10.08).

A similar process was also used to form GdZn$_{16}$(quinHA)$_{16}$(OTf)$_3$ (i.e., Gd$^{3+}$[12-MC-4]$_2$[24-MC-8] with (OTf)$_3$, 4 water molecules, and 4 DMF molecules) (67 mg, 39%), except that gadolinium triflate (79 mg, 0.13 mmol) was used. ESI-MS, calc. for [M]$^{3+}$, $C_{160}H_{96}GdN_{32}O_{32}Zn_{16}$, 1394.0; found 1393.2. Elem. Anal., calc. (found) for ($C_{163}H_{96}F_9GdN_{32}O_{41}S_3Zn_{16}$)($H_2O$)$_4$($C_3H_7NO$)$_4$, C: 42.09 (41.84), H: 2.66 (3.03), N: 10.10 (10.26).

A similar process was also used to form TbZn$_{16}$(quinHA)$_{16}$(OTf)$_3$ (i.e., Tb$^{3+}$[12-MC-4]$_2$[24-MC-8] with (OTf)$_3$, 5 water molecules, and 3 DMF molecules) (39 mg, 23%), except that terbium triflate (79 mg, 0.13 mmol) was used. ESI-MS, calc. for [M]$^{3+}$, $C_{160}H_{96}N_{32}O_{32}TbZn_{16}$, 1394.5; found 1394.1. Elem. Anal., calc. (found) for ($C_{163}H_{96}F_9N_{32}O_{41}S_3TbZn_{16}$)($H_2O$)$_5$($C_3H_7NO$)$_3$, C: 41.82 (41.50), H: 2.59 (2.71), N: 9.92 (9.90).

A similar process was also used to form EuZn$_{16}$(quinHA)$_{16}$(OTf)$_3$ (i.e., Eu$^{3+}$[12-MC-4]$_2$[24-MC-8] with (OTf)$_3$, 7 water molecules, and 1 DMF molecule) (69 mg, 40%), except that europium triflate (78 mg, 0.13 mmol) was used. ESI-MS, calc. for [M]$^{3+}$, $C_{160}H_{96}EuN_{32}O_{32}Zn_{16}$, 1392.2; found 1391.8. Elem. Anal., calc. (found) for ($C_{163}H96EuF_9N_{32}O_{41}S_3Zn_{16}$)($H_2O$)$_7$($C_3H_7NO$), C: 41.34 (41.00), H: 2.45 (2.90), N: 9.58 (9.80).

A similar process was also used to form ErZn$_{16}$(quinHA)$_{16}$(OTf)$_3$ (i.e., Er$^{3+}$[12-MC-4]$_2$[24-MC-8] with (OTf)$_3$, 5 water molecules, and 3 DMF molecules) (35 mg, 20%), except that erbium triflate (80 mg, 0.13 mmol) was used. ESI-MS, calc. for [M]$^{3+}$, $C_{160}H_{96}ErN_{32}O_{32}Zn_{16}$, 1397.3; found 1397.1. Elem. Anal., calc. (found) for ($C_{163}H_{96}ErF_9N_{32}O_{41}S_3Zn_{16}$)($H_2O$)$_5$($C_3H_7NO$)$_3$, C: 41.15 (41.49), H: 2.71 (2.86), N: 9.76 (10.16).

Photophysical Measurements

Luminescence data were collected on samples that were placed into 2.4 mm i.d. quartz capillaries or quartz Suprasil cells. Emission and excitation spectra were measured on a Horiba-Jobin-Yvon Fluorolog 3 spectrofluorimeter equipped with either a visible photomultiplier tube (PMT) (220-800 nm, R928P; Hamamatsu), a NIR solid-state InGaAs detector cooled to 77 K (800-1600 nm, DSS-IGA020L; Jobin-Yvon), or NIR PMTs (950-1450 nm, H10330-45; 950-1650 nm, H10330-75; Hamamatsu). All spectra were corrected for instrumental functions.

Luminescence lifetimes were determined under excitation at 355 nm provided by a Nd:YAG laser (YG 980; Quantel), while the signal was detected in the NIR by the aforementioned PMT (H10330-75). The output signal from the detectors was then fed to a 500 MHz bandpass digital oscilloscope (TDS 754C; Tektronix) and then transferred to a PC for treatment with Origin 8®. Luminescence lifetimes are averages of at least three independent measurements.

Quantum yields in the NIR were determined with a Fluorolog 3 spectrofluorimeter according to an absolute method using an integration sphere (GMP SA). Each sample was measured several times under slightly different experimental conditions. Estimated experimental error for quantum yields determination is 10%.

Photophysical Properties

Figure 2:
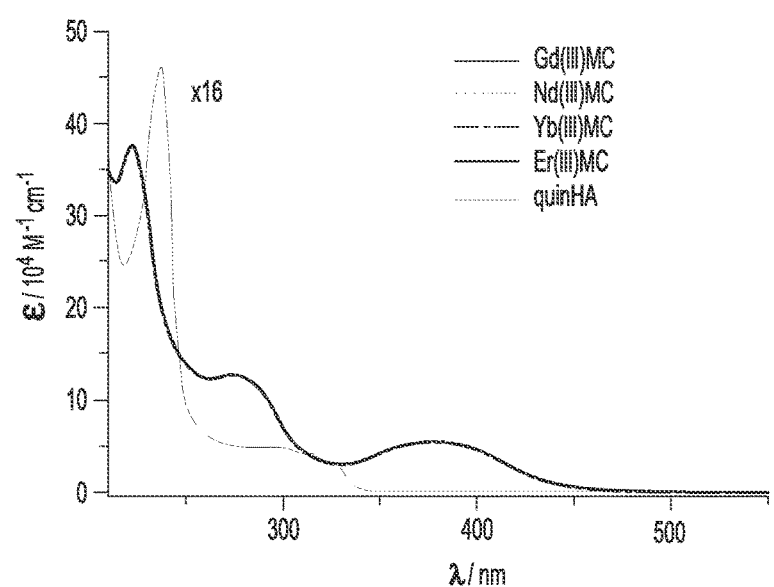
FIG. 2 is a graph of the absorption spectra of Ln(III) MC complexes ($2.04 \cdot 10^{-5}$ M, Ln(III)=Gd, Nd, Yb, Er) and quinaldichydroxamic acid (quinHA) ($2.42 \cdot 10^{-4}$ M) in methanol at 298 K, where the absorption spectrum of quinHA was multiplied by 16 times.

The ligand quinHA exhibits several absorption bands in the UV region due to $\pi^* \leftarrow \pi$ transitions within the quinoline moiety. As shown in FIG. 2, the long wavelength absorption cutoff is located at 340 nm. Upon deprotonation and formation of the metallacrown framework, Ln(III)[12-MC-4]2 [24-MC-8], a broad absorption appears in the near-visible region with an apparent maximum at 380 nm ($\varepsilon \approx 5.5 \cdot 10^4$ M$^{-1}$ cm$^{-1}$) and cutoff at 470 nm. In FIG. 2, the results are shown for the Gd(III), Nd(III), Yb(III), and Er(III). These results indicate, given that Zn(II) does not participate in either metal-to-ligand charge transfer (MLCT) or ligand-to-metal charge transfer (LMCT) and that absorption spectra are independent of the choice of lanthanide(III) ion, that this band is believed to be attributed to a ligand-based charge transfer of the quinHA ligand.

Figure 3:
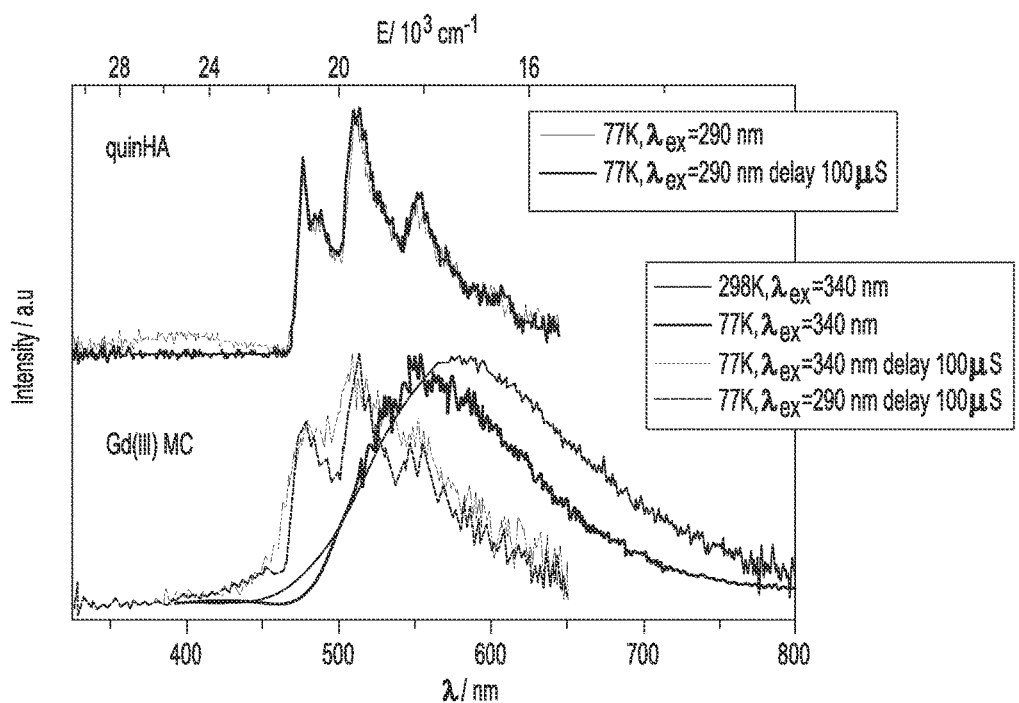
FIG. 3 is a graph depicting the corrected and normalized emission spectra of quinHA (10 mg/mL) under excitation at 290 in methanol at 77 K and Gd(III) MC (10 mg/mL) under excitation at 290 nm or 340 nm in methanol at 298 K and 77 K.

As illustrated in FIG. 3, upon UV excitation at 290 nm at room temperature, quinHA did not display any detectable emission. At 77 K, strong green luminescence centered at 510 nm with a weak band in the 325-460 nm range. The latter band disappeared upon enforcing a delay of 100 µs, so it can be assigned to a short-lived fluorescence while the green emission is phosphorescence. The energy of the triplet state of quinHA, determined on the 0-0 transition, can therefore be estimated as 21 000 cm−1 (476 nm).

Figure 4:
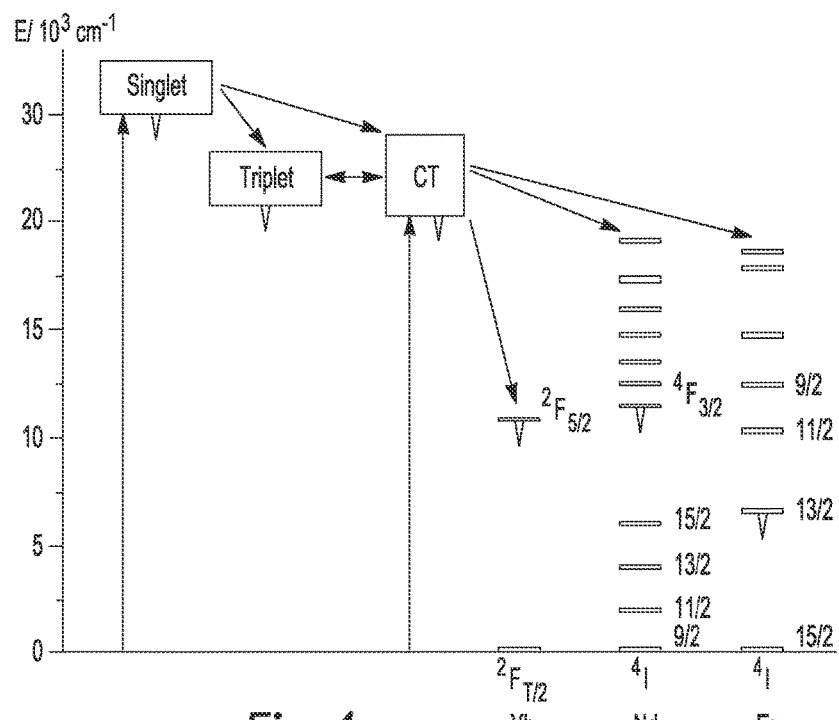
FIG. 4 is a simplified diagram of the energy migration processes in $Ln(III)[12\text{-}MC\text{-}4]_2[24\text{-}MC\text{-}8]$ metallacrown complexes when the metallacrown is formed using the quinaldichydroxamic acid (CT=ligand-based charge transfer states)

The energy gap between ground and excited states for Gd(III) is very high and, therefore, it is impossible for the Gd(III) ion in the corresponding metallacrown complex to be sensitized with 300-400 nm excitation. It is believed that this feature can be used to determine the energy levels of the metallacrown complexes in the absence of energy transfer to the Ln(III) ion. The Gd(III) metallacrown complex was exposed to UV excitation into the ligand-based charge transfer band at 340 nm at room temperature, resulting in a weak broad-band emission with a maximum at 580-590 nm (FIG. 3). Lowering the temperature to 77 K led to a slight sharpening of the band and a shift of the maximum to 545-555 nm (FIG. 3). As illustrated in FIG. 3, a further blue shift to 510 nm was observed upon application of a time delay of 100 µs. The position of the triplet state determined from the spectrum of Gd(III) metallacrown complex was the same as for quinHA within experimental error, 20 920 cm$^{-1}$ (478 nm). The position of the lowest excited singlet and the ligand-based charge transfer (CT) states were determined from the intersection of the absorption and emission (fluorescence) spectra of quinHA and Gd$^{3+}$[12-MC-4]$_2$[24-MC-8], respectively, and found to be located at 29 850 cm$^{-1}$ (335 nm) and 21 560 cm$^{-1}$ (565 nm). A proposed schematic diagram of the quinHA ligand's energy levels (singlet, triplet and CT) with respect to the energy levels of Yb(III), Nd(III) and Er(III) lanthanide ions and possible energy migration paths are shown in FIG. 4.

Figure 5:
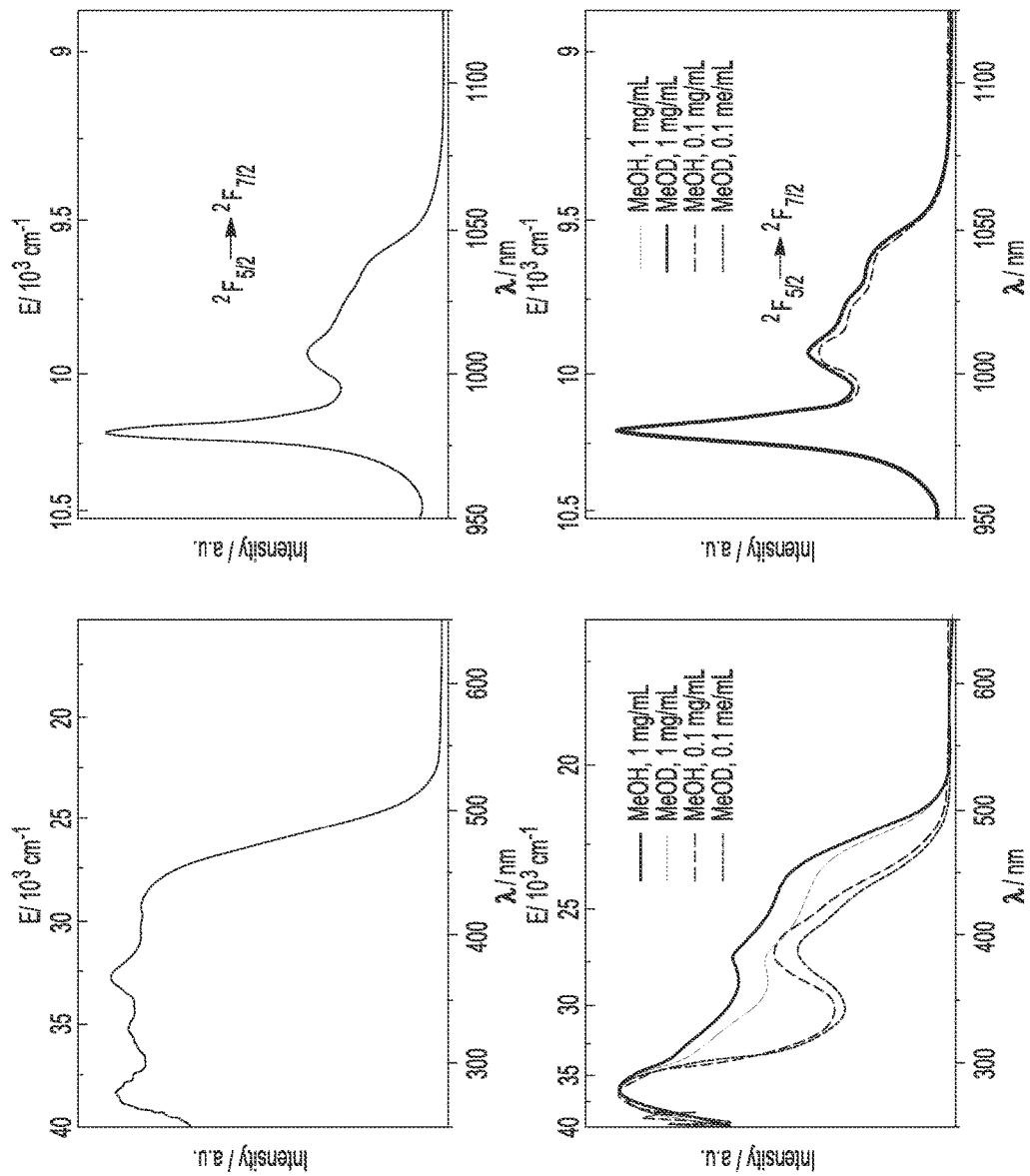
FIG. 5 illustrates spectra for a Yb(III) metallacrown complex, where the spectra on the left are the corrected and normalized excitation ($\lambda_{em}$=980 nm) spectra, and the spectra on the right are the corrected and normalized emission (under ligand excitation at 420 nm or 370 nm) spectra, and where the spectra on the top are the complex in the solid state, and the spectra on the bottom are the complex in methanol solutions.
Figure 6:
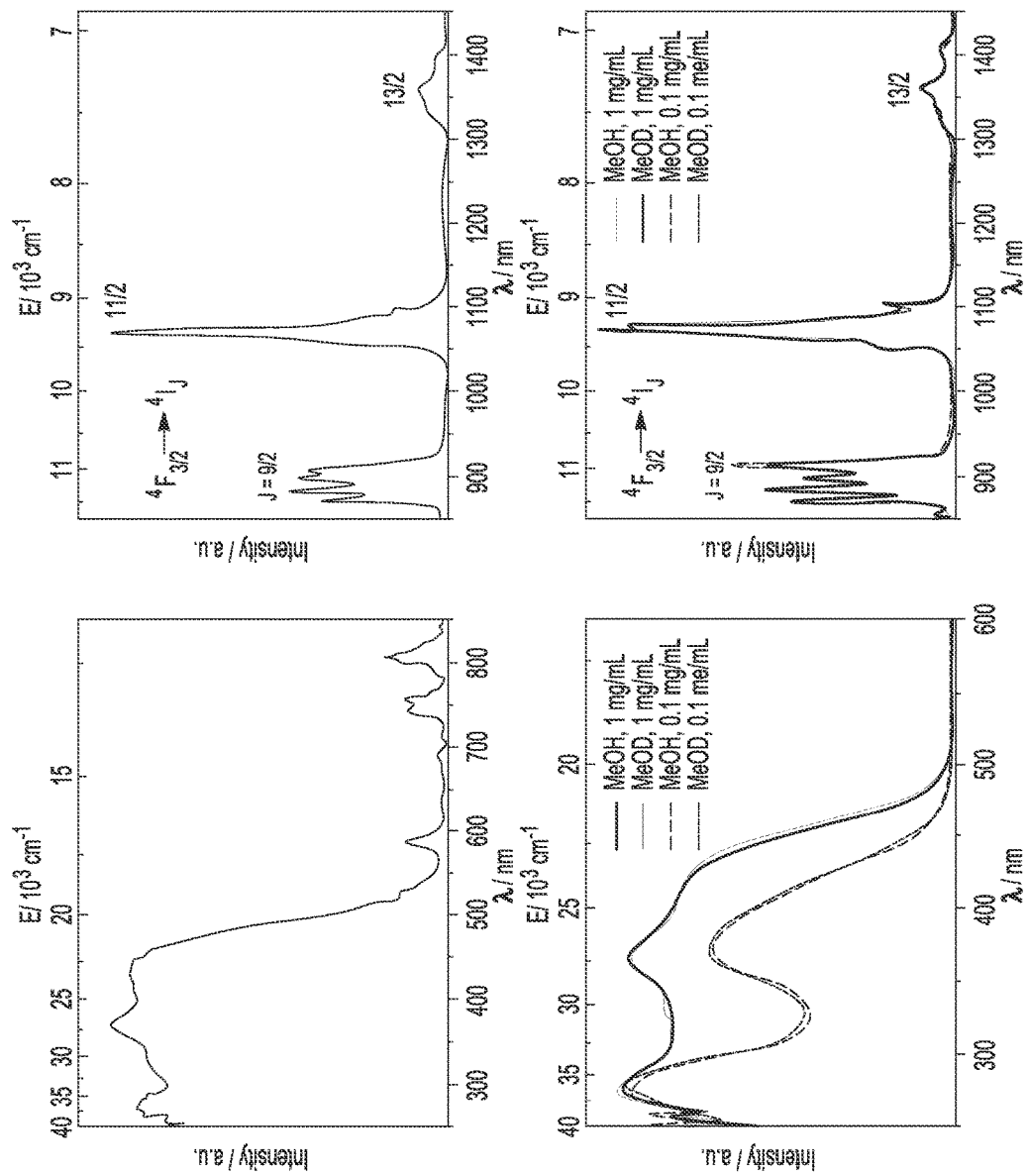
FIG. 6 illustrates spectra for a Nd(III) metallacrown complex, where the spectra on the left are the excitation ($\lambda_{em}$=1064 nm) spectra, and the spectra on the right are the emission (under ligand excitation at 420 nm or 370 nm) spectra, and where the spectra on the top are the complex in the solid state, and the spectra on the bottom are the complex in methanol solutions.
Figure 7:
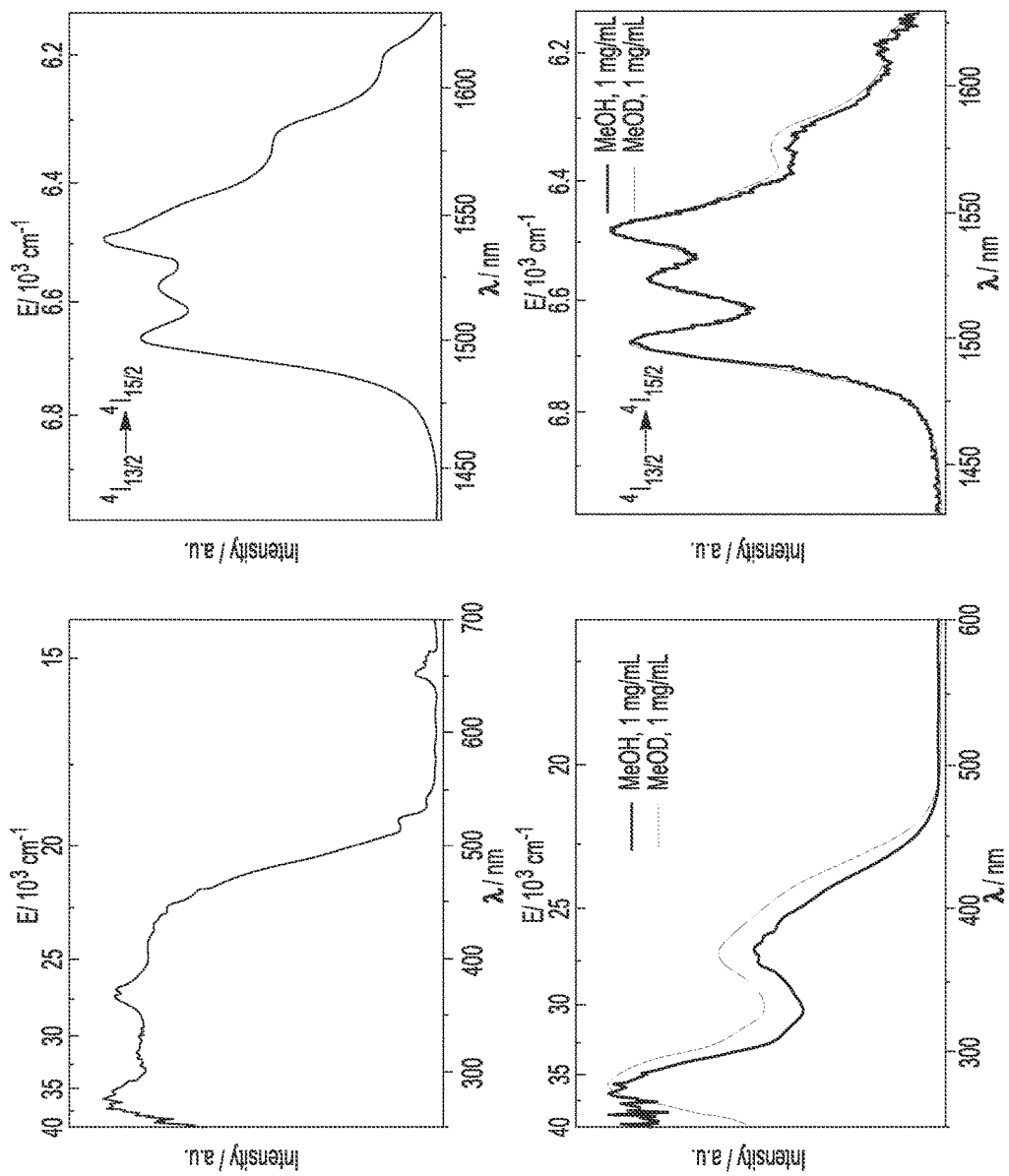
FIG. 7 illustrates spectra for an Er(III) metallacrown complex, where the spectra on the left are the excitation ($\lambda_{em}$=1525 nm) spectra, and the spectra on the right are the emission (under ligand excitation at 370 nm) spectra, and where the spectra on the top are the complex in the solid state, and the spectra on the bottom are the complex in methanol solutions.

Luminescence spectra were recorded for the Ln(III) metallacrown complexes (Ln(III)=Yb, Nd, Er) in the solid state and in solution (CH$_3$OH/CD$_3$OD) using excitation at 420 nm or 370 nm. All of the studied metallacrown complexes exhibit characteristic emission in the NIR range arising from the $_2F_{5/2} \rightarrow _2F_{7/2}$ (FIG. 5), $_4F_{3/2} \rightarrow _4I_J$ (J=9/2, 11/2, 13/2) (FIG. 6), and $_4I_{13/2} \rightarrow _4I_{15/2}$ (FIG. 7) transitions for the Yb$_{3+}$, Nd$_{3+}$, Er$_{3+}$ compounds, respectively. Excitation spectra of diluted methanol solutions (0.1 mg/mL) match well the corresponding absorption spectra (see FIG. 2), while an expansion of the band toward longer wavelengths was observed with increasing concentration (1 mg/mL) and for solid state samples. The quantitative photophysical parameters are summarized in Table 1.

TABLE 1

| Compound | State/Solvent[a] | Concentration | $\tau_{obs}$/µs | q[b] | $Q_{Ln}$/%L |
|---|---|---|---|---|---|
| Yb(III)MC | Solid | | 47.8(4) | | 2.44(4) |
| | CH$_3$OH | 1 mg/mL | 14.88(1) | 0 | 0.25(1) |
| | | 0.1 mg/mL | 15.14(4) | 0 | 0.27(1) |

TABLE 1-continued

| Compound | State/Solvent[a] | Concentration | $\tau_{obs}/\mu s$ | $q^b$ | $Q_{Ln/\%}^L$ |
|---|---|---|---|---|---|
| | CD₃OD (i.e., methanol-d₄) | 1 mg/mL | 150.7(2) | | 2.88(2) |
| | | 0.1 mg/mL | 144.6(5) | | 2.91(7) |
| Nd(III)MC | Solid | | 1.79(2) | | 1.13(4) |
| | CH₃OH | 1 mg/mL | 1.16(1) | 0 | 0.38(1) |
| | | 0.1 mg/mL | 1.16(1) | 0 | 0.40(1) |
| | CD₃OD | 1 mg/mL | 4.11(3) | | 1.35(1) |
| | | 0.1 mg/mL | 4.00(1) | | 1.38(1) |
| Er(III)MC | Solid | | 5.73(2) | | $4.2(1) \cdot 10^{-2}$ |
| | CH₃OH | 1 mg/mL | 1.25(1) | | $9.9(3) \cdot 10^{-4}$ |
| | CD₃OD | 1 mg/mL | 11.40(3) | | $3.60(6) \cdot 10^{-2}$ |

[a] Data for 298 K under excitation at 370 nm for quantum yields and 355 nm for lifetimes. Standard deviation (2σ) between parentheses; estimated relative errors: $\tau_{obs}$, ±2%; $Q_{Ln}^L$, ±10%.
[b] The inner sphere hydration numbers were calculated according to the following equations: $q_{Yb} = 2 \times (k_{CH3OH} - k_{CD3OD} - 0.1)$ (in μs) and $q_{Nd} = 290 \times (k_{CH3OH} - k_{CD3OD}) - 0.4$ (in ns)

The quantum yields for the Nd(III) and Er(III) metallacrown complexes, in the solid state and in deuterated methanol (i.e., CD₃OD, methanol-d₄), are believed to be the highest reported to date among lanthanide compounds with C—H containing organic ligands. The quantum yield of the Yb(III) metallacrown complex was close to the largest published values.

NIR Epifluorescence Microscopy Using Yb(III) Metallacrowns

To demonstrate the ability of the lanthanide(III) metallacrown complexes to sustain and operate as optical imaging agents in biological conditions, two epifluorescence microscopy experiments on HeLa (Human Epithelial Ovarian Carcinoma) cells were performed and are described below. The preparation of the Yb(III) Metallacrowns and the description of the NIR Epifluorescence Microscopy are applicable for both experiments.

Preparation of Yb(III) Metallacrown Solution or Beads

Yb³⁺[12-MC-4]₂[24-MC-8] was prepared as described above, and was dissolved in DMSO at an appropriate concentration, and was used as such or was incubated with beads for incorporation therein.

NIR Epifluorescence Microscopy Observations

NIR epifluorescence microscopy was performed with an Axio Observer Z1 fluorescence inverted microscope (Zeiss, Le Pecq, France) equipped with an EMCCD Evolve 512 photometric camera (Roper Scientific). The EMCCD Evolve 512 photometric camera was linked to a computer driving the acquisition software Axiovision (Zeiss). The inverted microscope was equipped with Zeiss objectives (immersion Plan Apochromat 63x (Numerical Aperture (NA)=1.4), Plan Neofluar 40x (NA=0.75), Plan Apochromat 20x (NA=0.8)). A Zeiss HXP-120 light source (metal halide) was used as the excitation system, and was combined with a UV cube filter unit as follows: 377 nm band pass 50 nm filter for excitation, and long pass 805 nm filter for Yb(III) emission in the NIR range.

NIR Epifluorescence Microscopy—Experiment 1

HeLa cells were obtained from ATCC (Molsheim, France), and were grown at 37° C. in a 5% CO₂ humidified atmosphere. Every 3 to 4 days, 5×10⁵ cells were seeded into a 25 cm² plastic flask. Cells were cultivated in Mimimum Essential Medium (MEM) supplemented with 10% fetal bovine serum (FBS), 1% penicillin/streptomycin and 1% L-glutamine, and with 1% of a 100x non-essential amino acid solution. 7×10³ cells were seeded in 8 well Lab Tek Chamber coverglass (Nunc, Dutsher S. A., Brumath, France) one day before the experiment.

Some of the cells were then incubated with 1 μM of Yb³⁺[12-MC-4]₂[24-MC-8] diluted in Opti-MEM® Medium (Invitrogen Corporation) supplemented with 2% FBS and 1% of dimethyl sulfoxide (DMSO). After 24 hours at 37° C., cells were rinsed twice with cold phosphate buffered saline (PBS) and the cell culture media was changed and replaced by Opti-MEM® media exempt of phenol red. For a control, other HeLa cells were treated in the same way but without the addition of Yb³⁺[12-MC-4]₂[24-MC-8]. These cells are referred to herein as untreated cells.

Figure 8A:
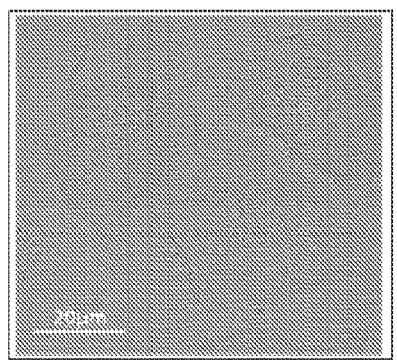
FIGS. 8A and 8B are black and white representations of images, obtained using near infrared (NIR) epifluorescence microscopy, of human epithelial ovarian carcinoma (HeLa) cells after 24 hours of incubation with 1 μM of Yb(III) metallacrown complex, where
Figure 8B:
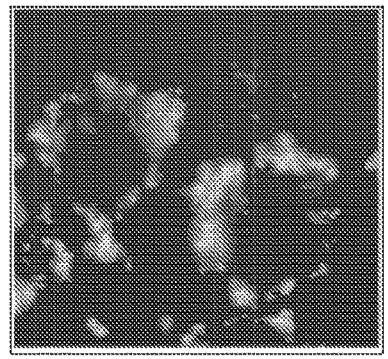
Figure 8C:
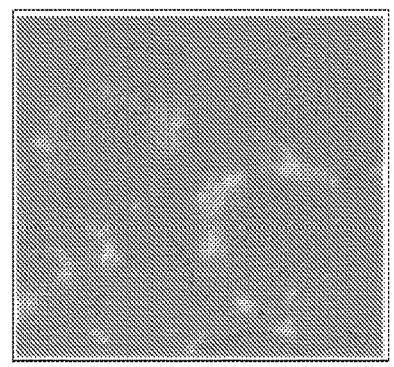
FIG. 8C is the merged image of FIGS. 8A and 8B.
Figure 8D:
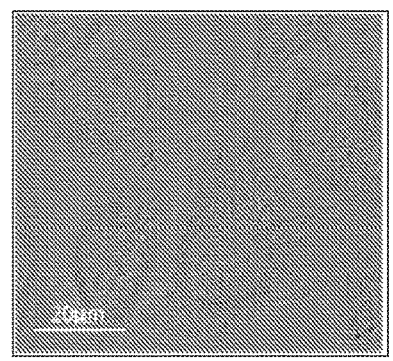
FIGS. 8D and 8E are black and white representations of images, obtained using NIR epifluorescence microscopy, of untreated HeLa cells, where
Figure 8E:
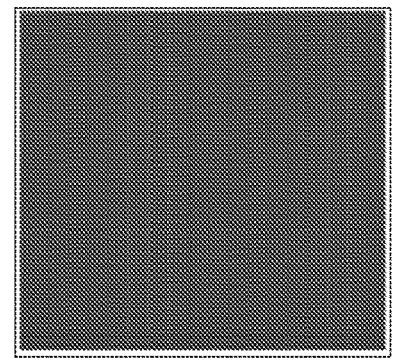
Figure 8F:
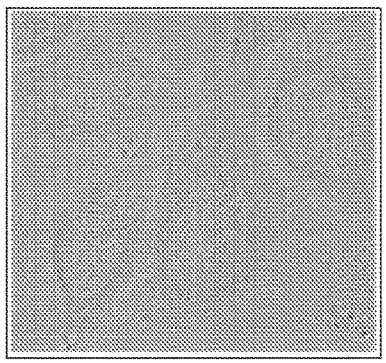
FIG. 8F is the merged image of FIGS. 8D and 8E.

NIR Epifluorescence Microscopy was used to observe the treated cells after 24 hours of incubation with Yb³⁺[12-MC-4]₂[24-MC-8] and the untreated cells. Images of the treated and untreated cells were obtained upon exposure to a brightfield, and upon exposure to excitation ($\lambda_{ex}$=377 nm with 50 nm band pass filter). FIG. 8A is the brightfield image and FIG. 8B is the emission signal image of the treated cells in the NIR range (long pass 805 nm filter) obtained after 500 ms of exposure to excitation. FIG. 8C is FIGS. 8A and 8B merged together. Upon excitation of the HeLa cells incubated with Yb³⁺[12-MC-4]₂[24-MC-8], the emission in the NIR range was unambiguously detected. This was in contrast to the untreated cells. FIG. 8D is the brightfield image and FIG. 8E is the emission signal image of the untreated cells in the NIR range (long pass 805 nm filter) obtained after 500 ms of exposure to excitation. FIG. 8F is FIGS. 8D and 8E merged together. As illustrated in both FIGS. 8E and 8F, the emission in the NIR range for the untreated HeLa cells was not detected.

NIR Epifluorescence Microscopy—Experiment 2

The HeLa cell line obtained from ATCC (Molsheim, France) was cultured in Dulbecco's modified Eagle's medium (DMEM) supplemented with 10% heat-inactivated fetal bovine serum (FBS), 1% of 100xnon-essential amino-acid solution, 1% of L-glutamine (GlutaMAX) and 1% of streptomycin/penycilin antibiotics. The cells were seeded in a 8-well Lab Tek Chamber coverglass (Nunc, Dutsher S. A., Brumath, France) at a density of 3×104 cells/well and cultured at 37° C. in 5% humidified CO₂ atmosphere. After 24 hours, the cell culture media was removed, and the cells were washed twice with ice-cold Opti-MEM®. Some of the cells were incubated with a 5 μM solution of Yb³⁺[12-MC-4]₂[24-MC-8] in Opti-MEM® media supplemented with 2% of FBS at 37° C. in 5% CO₂ atmosphere for 11 hours or 12 hours. Other cells were incubated with beads incorporating the Yb³⁺[12-MC-4]₂[24-MC-8] in OPTIMEM media supplemented with 2% of FBS at 37° C. in 5% CO2 atmosphere for 11 hours or 12 hours. Prior to epifluorescent imaging the cells were washed twice with ice-cold PBS or/and ice-cold PBS with 1% Tween 20 in order to remove any non-specifically bound metallacrowns.

Figure 9A:
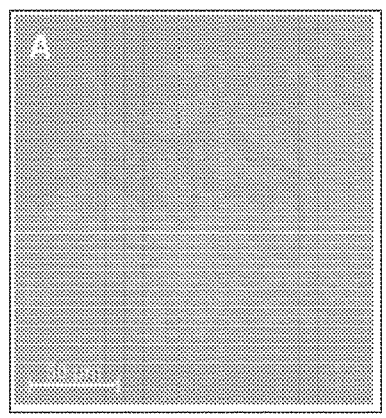
FIGS. 9A and 9B are black and white representations of images, obtained using NIR epifluorescence microscopy, of HeLa cells after 12 hours of incubation with 5 μM of Yb(III) metallacrown complex, where
Figure 9B:
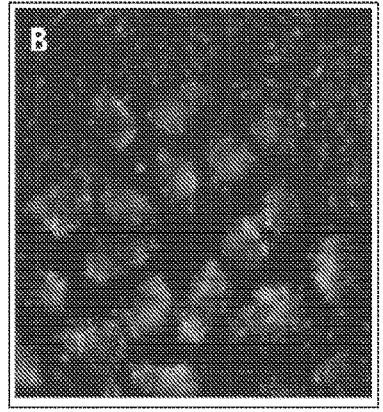
Figure 9C:
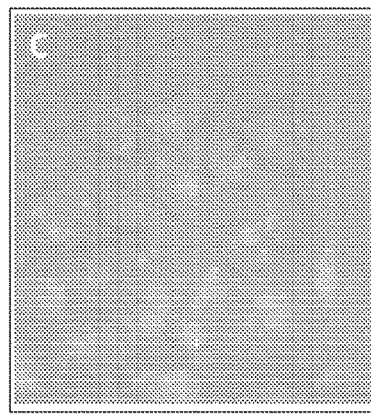
FIG. 9C is the merged image of FIGS. 9A and 9B.

NIR Epifluorescence Microscopy was used to observe the cells treated in the 5 μM solution of Yb³⁺[12-MC-4]₂[24-MC-8] after 12 hours. Exposure to the excitation wavelength was for 800 ms. The brightfield image is shown in FIG. 9A, the emission image is shown in FIG. 9B, and the merged images (9A and 9B) are shown in FIG. 9C.

Figure 10A:
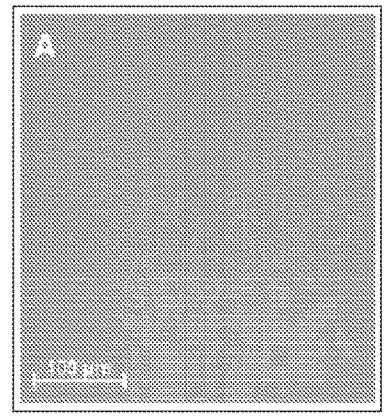
FIGS. 10A and 10B are black and white representations of images, obtained using NIR epifluorescence microscopy, of HeLa cells after 11 hours of incubation with beads containing Yb(III) metallacrown complex, where
Figure 10B:
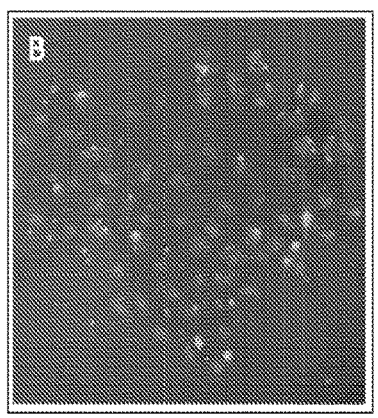
Figure 10C:
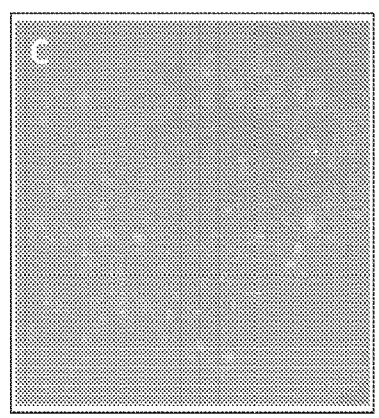
FIG. 10C is the merged image of FIGS. 10A and 10B.

NIR Epifluorescence Microscopy was used to observe the cells treated with the beads containing Yb³⁺[12-MC-4]₂[24-MC-8] after 11 hours. Exposure to the excitation wavelength was for 13 s. The brightfield image is shown in FIG. 10A, the emission image is shown in FIG. 10B, and the merged images (10A and 10B) are shown in FIG. 10C.

Figure 11A:
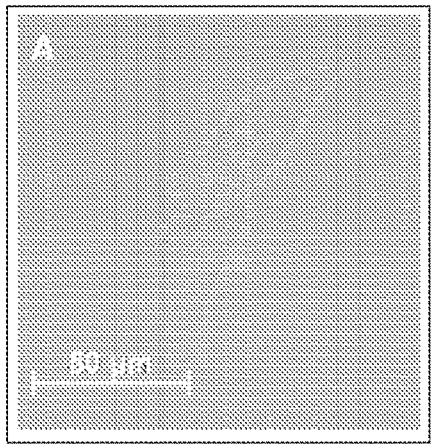
FIGS. 11A and 11B are black and white representations of images, obtained using NIR epifluorescence microscopy, of HeLa cells after 11 hours of incubation with beads containing Yb(III) metallacrown complex, where
Figure 11B:
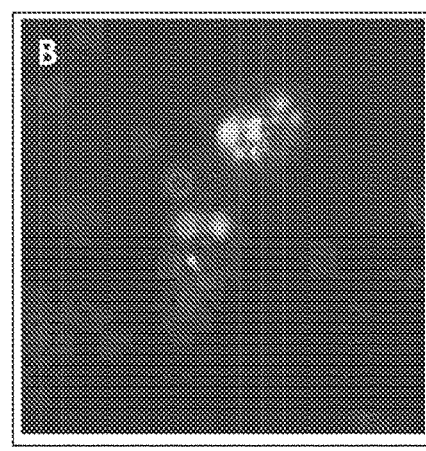
Figure 11C:
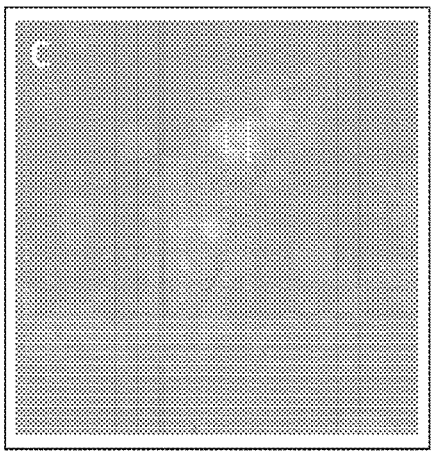
FIG. 11C is the merged image of FIGS. 11A and 11B.

NIR Epifluorescence Microscopy was also used to observe the cells treated in the beads containing Yb³⁺[12-MC-4]₂[24-MC-8] after 11 hours. Exposure to the excitation wavelength was for 8 s. The brightfield image is shown in FIG. 11A, the emission image is shown in FIG. 11B, and the merged images (11A and 11B) are shown in FIG. 11C.

In both NIR Epifluorescence Microscopy experiments, Yb(III) emission in the NIR range of the treated cells incubated with Yb$^{3+}$[12-MC-4]$_2$[24-MC-8] was unambiguously detected using short exposure times. Experiments 1 and 2 demonstrate that Yb$^{3+}$[12-MC-4]$_2$[24-MC-8] can be used in experimental conditions suitable for living HeLa cells. The observations of Yb$^{3+}$[12-MC-4]$_2$[24-MC-8] emission with short exposure times confirms that these compounds can operate in biological conditions without loss of luminescence efficiency. As such, highly sensitive detection may be performed in the NIR range using the metallacrown complexes disclosed herein.

The lanthanide metallacrown complexes disclosed herein are unique at least in part because they exhibit absorption over a broad range of UV-visible wavelengths due to ligand-based transitions (including the ligand-based charge transfer state). NIR luminescence from the Ln(III) ions is believed to be sensitized through the excitation of these ligand transitions. In addition, the specific structure of the lanthanide metallacrown complexes is versatile and can have a relatively large distance between the Ln(III) ion and the organic ligand.

It is to be understood that the ranges provided herein include the stated range and any value or sub-range within the stated range. For example, a range from about 12 hours to about 24 hours should be interpreted to include not only the explicitly recited limits of about 12 hours to about 24 hours, but also to include individual values, such as 14.25 hours, 16 hours, 21.5 hours, etc., and sub-ranges, such as 15 hours to 20 hours, etc. Furthermore, when "about" is utilized to describe a value, this is meant to encompass minor variations (up to +/−5%) from the stated value.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

In describing and claiming the examples disclosed herein, the singular forms "a", "an", and "the" include plural referents unless the context clearly dictates otherwise.

While several examples have been described in detail, it will be apparent to those skilled in the art that the disclosed examples may be modified. Therefore, the foregoing description is to be considered non-limiting.

What is claimed is:

1. A metallacrown complex, having the formula: Ln(III)[12-MC-4]2[24-MC-8], wherein MC is a metallacrown macrocycle with a repeating sub-unit consisting of a transition metal ion (M(II)) and a hydroxamic acid (HA) ligand that produces a ligand-based charge transfer state when incorporated into the metallacrown complex;

wherein the hydroxamic acid ligand has the structure:

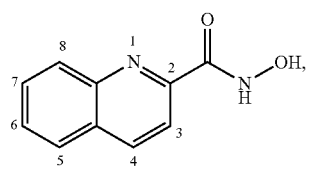 [SMILES: O=C(NO)c1ccc2ccccc2n1]

wherein the Ln(III) is selected from the group consisting of Y$^{3+}$, La$^{3+}$, Ce$^{3+}$, Pr$^{3+}$, Nd$^{3+}$, Pm$^{3+}$, Sm$^{3+}$, Eu$^{3+}$, Gd$^{3+}$, Tb$^{3+}$, Dy$^{3+}$, Ho$^{3+}$, Er$^{3+}$, Tm$^{3+}$, Yb$^{3+}$, and Lu$^{3+}$, and wherein the transition metal ion is selected from the group consisting of Co$^{2+}$, Ni$^{2+}$, Cu$^{2+}$, Zn$^{2+}$, Rh$^{2+}$, Pd$^{2+}$, Ag$^{2+}$, Cd$^{2+}$, Ir$^{2+}$, Pt$^{2+}$, Au$^{2+}$, and Hg$^{2+}$.

2. The metallacrown complex as defined in claim 1 wherein:
   each [12-MC-4] unit includes four repeating [M(II)HA] sub-units that form a macrocyclic ring having twelve total atoms; and
   the [24-MC-8] unit includes eight repeating [M(II)HA] sub-units that form a macrocyclic ring having twenty-four total atoms.

3. The metallacrown complex as defined in claim 1 wherein a charge balance of the metallacrown complex is obtained with a negatively charged species.

4. The metallacrown complex as defined in claim 3 wherein the negatively charged species is an unbound counterion selected from the group consisting of a triflate, a mesylate, a besylate, a camsylate, an edisylate, an estolate, an esylate, a napsylate, a tosylate, a fluoride, a chloride, a bromide, an iodide, a nitrate, a sulfate, a carbonate, an acetate, a phosphate, or a sulfonate.

5. The metallacrown complex as defined in claim 1 wherein:
   the Ln(III) is a coordinate central metal;
   four inward facing hydroximate oxygen atoms of each of the two [12-MC-4] units coordinate to the coordinate central metal to form a sandwich complex; and
   the sandwich complex is bound within a cavity of the [24-MC-8] unit through bridging oxygen atoms.

6. A method for making a metallacrown complex, comprising:
   dissolving a hydroxamic acid (HA) ligand that is to produce a ligand-based charge transfer state when incorporated into the metallacrown complex, a transition metal salt, and a rare-earth salt in a solvent to form a solution, wherein the hydroxamic acid ligand has the structure:

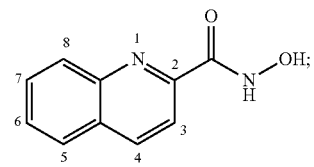

adding a base to the solution;
   stirring the solution at a predetermined temperature for a predetermined time; and
   exposing the solution to a purification method, thereby producing crystals of the metallacrown complex.

7. The method as defined in claim 6 wherein the solvent is selected from the group consisting of dimethylformamide, methanol, water, and combinations thereof.

8. The method as defined in claim 6 wherein the purification method is recrystallization by slow evaporation of the solvent, recrystallization by vapor diffusion, recrystallization by solvent layering, high-performance liquid chromatography, or flash chromatography.

9. The method as defined in claim 6 wherein:
   the transition metal salt includes any of Co$^{2+}$, Ni$^{2+}$, Cu$^{2+}$, Zn$^{2+}$, Rh$^{2+}$, Pd$^{2+}$, Ag$^{2+}$, Cd$^{2+}$, Ir$^{2+}$, Pt$^{2+}$, Au$^{2+}$, or Hg$^{2+}$ and any of a triflate, a mesylate, a besylate, a camsylate, an edisylate, an estolate, an esylate, a napsylate, a tosylate, a fluoride, a chloride, a bromide, an iodide, a nitrate, a sulfate, a carbonate, an acetate, a phosphate, or a sulfonate as a counterion; and the rare-earth salt includes any of Sc$^{3+}$, Y$^{3+}$, La$^{3+}$, Ce$^{3+}$, Pr$^{3+}$, Nd$^{3+}$, Pm$^{3+}$, Sm$^{3+}$, Eu$^{3+}$, Gd$^{3+}$, Tb$^{3+}$, Dy$^{3+}$, Ho$^{3+}$, Er$^{3+}$, Tm$^{3+}$, Yb$^{3+}$, or Lu$^{3+}$ and any of a triflate, a mesylate, a besylate, a camsylate, an edisylate, an estolate, an esylate, a napsylate, a tosylate, a fluoride, a chloride, a bromide, an iodide, a nitrate, a sulfate, a carbonate, an acetate, a phosphate, or a sulfonate as a counterion.

10. The method as defined in claim 6, further comprising dissolving the crystals of the metallacrown complex in a solvent to form a solution, the solvent being selected from the group consisting of water, dimethylsulfoxide, methanol, dimethylformamide, and ethanol.

11. The method as defined in claim 10, further comprising:
   incubating polymer beads in the solution including the dissolved crystals of the metallacrown complex, thereby incorporating the metallacrown complex into the polymer beads; and
   collecting metallacrown complex loaded polymer beads by centrifugation and decanting.

12. An optical imaging agent, comprising:
   a carrier; and
   a metallacrown complex incorporated into the carrier, the metallacrown having the formula: Ln(III)[12-MC-4]2[24-MC-8], wherein MC is a metallacrown macrocycle with a repeating sub-unit consisting of a transition metal ion (M(II)) and a hydroxamic acid (HA) ligand that produces a ligand-based charge transfer state when incorporated into the metallacrown complex, wherein the hydroxamic acid ligand has the structure:

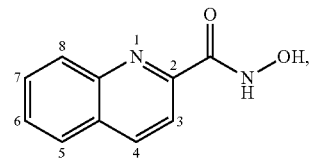 [SMILES: O=C(NO)c1ccc2ccccc2n1]

wherein the Ln(III) is selected from the group consisting of Y$^{3+}$, La$^{3+}$, Ce$^{3+}$, Pr$^{3+}$, Nd$^{3+}$, Pm$^{3+}$, Sm$^{3+}$, Eu$^{3+}$, Gd$^{3+}$, Tb$^{3+}$, Dy$^{3+}$, Ho$^{3+}$, Er$^{3+}$, Tm$^{3+}$, Yb$^{3+}$, and Lu$^{3+}$, and
   wherein the transition metal ion is selected from the group consisting of Co$^{2+}$, Ni$^{2+}$, Cu$^{2+}$, Zn$^{2+}$, Rh$^{2+}$, Pd$^{2+}$, Ag$^{2+}$, Cd$^{2+}$, Ir$^{2+}$, Pt$^{2+}$, Au$^{2+}$, and Hg$^{2+}$.

13. The optical imaging agent as defined in claim 12 wherein the carrier is a solvent of the metallacrown complex.

14. The optical imaging agent as defined in claim 12 wherein the carrier is a polymer bead.

15. A method for using the optical imaging agent as defined in claim 12, the method comprising:
   incubating cells in a medium with the optical imaging agent for a predetermined time; and
   exposing the incubated cells to an optical imaging technique.

* * * * *